(12) United States Patent
DiFoggio et al.

(10) Patent No.: US 11,156,084 B2
(45) Date of Patent: Oct. 26, 2021

(54) OIL-BASED MUD CONTAMINATION ESTIMATE FROM PHYSICAL PROPERTIES

(71) Applicant: Baker Hughes, LLC, Houston, TX (US)

(72) Inventors: Rocco DiFoggio, Houston, TX (US); Hermanus J. Nieuwoudt, Tomball, TX (US)

(73) Assignee: BAKER HUGHES HOLDINGS LLC, Houston, TX (US)

( * ) Notice: Subject to any disclaimer, the term of this patent is extended or adjusted under 35 U.S.C. 154(b) by 104 days.

(21) Appl. No.: 16/430,283

(22) Filed: Jun. 3, 2019

(65) Prior Publication Data

US 2019/0301281 A1    Oct. 3, 2019

Related U.S. Application Data

(63) Continuation-in-part of application No. 16/155,820, filed on Oct. 9, 2018, which is a continuation-in-part
(Continued)

(51) Int. Cl.
*E21B 49/08* (2006.01)
*G01N 33/24* (2006.01)
(Continued)

(52) U.S. Cl.
CPC ............ *E21B 49/082* (2013.01); *E21B 47/12* (2013.01); *G01N 33/24* (2013.01); *G06F 17/18* (2013.01); *G16C 20/20* (2019.02)

(58) Field of Classification Search
CPC ................................ E21B 47/12; E21B 49/082
See application file for complete search history.

(56) References Cited

U.S. PATENT DOCUMENTS 5,377,755 A    1/1995  Michaels et al.
5,622,223 A    4/1997  Vasquez
(Continued)

OTHER PUBLICATIONS

J. Zou, et al., "A Breakthrough in Accurate Downhole Fluid Sample Contamination Prediction in Real-Time," SPWLA 56th Annual Logging Symposium, Jul. 18-22, 2015.
(Continued)

*Primary Examiner* — Caroline N Butcher
(74) *Attorney, Agent, or Firm* — Mossman Kumar & Tyler PC

(57) ABSTRACT

Methods and apparatus for estimating a presence of oil-based mud (OBM) in a downhole fluid. Methods include generating measurement values by measuring one or more gross physical properties of the downhole fluid with at least one sensor, the measurement values comprising at least one measurement value representative of each gross physical property; and estimating with at least one processor a relative concentration of OBM with respect to the downhole fluid by using a model correlating the measurement values with the relative concentration. Methods may include taking measurements from the downhole fluid in situ and/or estimating the relative concentration in real-time with respect to generating the measurement values. The model may comprise a correlation prediction function mapping the measurement values to the relative concentration, which may use the measurement values as input to predict the relative concentration.

21 Claims, 11 Drawing Sheets

Related U.S. Application Data of application No. 15/600,035, filed on May 19, 2017, now Pat. No. 10,094,213.

(51) Int. Cl.
*E21B 47/12* (2012.01)
*G16C 20/20* (2019.01)
*G06F 17/18* (2006.01)

(56) References Cited

U.S. PATENT DOCUMENTS

| | | | |
|---|---|---|---|
| 5,741,962 | A | 4/1998 | Birchak et al. |
| 6,609,568 | B2 | 8/2003 | Krueger et al. |
| 7,219,541 | B2 | 5/2007 | DiFoggio |
| 8,037,747 | B2 | 10/2011 | Difoggio |
| 9,228,429 | B2 * | 1/2016 | DiFoggio ............... E21B 47/103 |
| 2005/0216196 | A1 * | 9/2005 | Akkurt ................. G01N 24/081 702/6 |
| 2013/0180710 | A1 * | 7/2013 | DiFoggio ................ E21B 47/06 166/250.01 |
| 2015/0057935 | A1 | 2/2015 | Wu |
| 2017/0322191 | A1 * | 11/2017 | DiFoggio ............ G01N 30/8675 |
| 2018/0156035 | A1 | 6/2018 | Difoggio et al. |

OTHER PUBLICATIONS

J. Zuo et al., Advances in Quantification of Miscible Contamination in Hydrocarbon and Water Samples from Downhole to Surface Laboratories, SPWLA 58th Annual Logging Symposium, Jun. 17-21, 2017.

M. Nwume et al., "Geochemical Approach to Resolve Uncertainty in Quantifying Oil-Based-Mud OBM Contamination of Reservoir Fluids," SPE-193519-MS, Society of Petroleum Engineers.

P. Olapade, Predicting Reservoir Fluid Sample Contamination Using an Advanced Equation-of-State-Based Model, SPWLA 59th Annual Logging Symposium, Jun. 2-6, 2018.

R. DiFoggio, Examination of Some Misconceptions about Near-Infrared Analysis, Applied Spectroscopy Jan. 1995 49: 67-75, doi:10.1366/0003702953963247.

\* cited by examiner $$\begin{array}{llll} D^1 & V^0 & p^0 & T^0 \\ D^0 & V^1 & p^0 & T^0 \\ D^0 & V^0 & p^1 & T^0 \\ D^0 & V^0 & p^0 & T^1 \end{array} \quad \text{First Order}$$

FIG. 5A

$$\begin{array}{llll} D^2 & V^0 & p^0 & T^0 \\ D^1 & V^1 & p^0 & T^0 \\ D^1 & V^0 & p^1 & T^0 \\ D^1 & V^0 & p^0 & T^1 \\ D^0 & V^2 & p^0 & T^0 \\ D^0 & V^1 & p^1 & T^0 \\ D^0 & V^1 & p^0 & T^1 \\ D^0 & V^0 & p^2 & T^0 \\ D^0 & V^0 & p^1 & T^1 \\ D^0 & V^0 & p^0 & T^2 \end{array} \quad \text{Second Order}$$

FIG. 5B

$$\begin{array}{llll} D^3 & V^0 & p^0 & T^0 \\ D^2 & V^1 & p^0 & T^0 \\ D^2 & V^0 & p^1 & T^0 \\ D^2 & V^0 & p^0 & T^1 \\ D^1 & V^2 & p^0 & T^0 \\ D^1 & V^1 & p^1 & T^0 \\ D^1 & V^1 & p^0 & T^1 \\ D^1 & V^0 & p^2 & T^0 \\ D^1 & V^0 & p^1 & T^1 \\ D^1 & V^0 & p^0 & T^2 \\ D^0 & V^3 & p^0 & T^0 \\ D^0 & V^2 & p^1 & T^0 \\ D^0 & V^2 & p^0 & T^1 \\ D^0 & V^1 & p^2 & T^0 \\ D^0 & V^1 & p^1 & T^1 \\ D^0 & V^1 & p^0 & T^2 \\ D^0 & V^0 & p^3 & T^0 \\ D^0 & V^0 & p^2 & T^1 \\ D^0 & V^0 & p^1 & T^2 \\ D^0 & V^0 & p^0 & T^3 \end{array} \quad \text{Third Order}$$

FIG. 5C

Note that : 100% = C1wt% + C2wt% + C3wt% + C4wt% + C5wt% + C6wt% + C7pwt%

| | Methane C1wt% | Ethane C2wt% | Propane C3wt% | Butane C4wt% | Pentane C5wt% | Hexane C6wt% | Heptane+ C7wt% | Pressure P [psi] | Temperature T [C] | Compressibility C [1/Pa] | Viscosity V [cP] | Density D [g/cc] | Sound Speed s [m/s] |
|---|---|---|---|---|---|---|---|---|---|---|---|---|---|
| Minimum | 0.0237 | 0.0105 | 0.0000 | 0.000 | 0.0000 | 0.0000 | 30.6995 | 664 | 27 | 1.934E-11 | 0.025 | 0.188 | 13 |
| Maximum | 66.22345 | 9.0150 | 7.2541 | 6.5683 | 15.7586 | 15.7586 | 99.1163 | 15092 | 146 | 1.769E-04 | 898.000 | 0.951 | 2803 |
| Mean | 6.9897 | 1.6477 | 1.9646 | 1.8612 | 2.2663 | 2.2663 | 81.7998 | 4929 | 85 | 4.209E-07 | 7.959 | 0.693 | 890 |

FIG. 6

Regression Summary for Dependent Variable. C3wt
R= .78049089 $R^2$= .60916603 Adjusted $R^2$= .60373778
$F(7,504)$=112.22 $p<0.0000$ Std.Error of estimate: .87291

Regression Summary for Dependent Variable. C4wt
R= .78045690 $R^2$= .60911297 Adjusted $R^2$= .60367319
$F(7,503)$=111.97 $p<0.0000$ Std.Error of estimate: .75902

Regression Summary for Dependent Variable. C5wt
R= .80598259 $R^2$= .64960794 Adjusted $R^2$= .63971784
F(14,496)=65.683 p<0.0000 Std.Error of estimate: .60516

Regression Summary for Dependent Variable. C6wt
R= .80552325 $R^2$= .64886770 Adjusted $R^2$= .63970160
F(13,498)=70.790 p<0.0000 Std.Error of estimate: .82635

OIL-BASED MUD CONTAMINATION ESTIMATE FROM PHYSICAL PROPERTIES

CROSS-REFERENCE TO RELATED APPLICATIONS

This application is a Continuation-In-Part of U.S. patent application Ser. No.: 16/155,820, filed Oct. 9, 2018, which is a Continuation-In-Part of U.S. patent application Ser. No.: 15/600,035, filed May 19, 2017, now U.S. Pat. No.: 10,094,213, the entire disclosure of which is incorporated herein by reference in its entirety.

FIELD OF THE DISCLOSURE

This disclosure generally relates to downhole fluids, and in particular to methods and apparatuses for testing downhole fluids while drilling.

BACKGROUND OF THE DISCLOSURE

Drilling techniques for developing hydrocarbons in an earth formation are well-known. A borehole intersecting the formation is formed by rotation of a drill bit on the distal end of a drilling assembly. The borehole is typically filled with drilling fluid during the drilling process, referred to as drilling mud. The liquid part of a drilling mud that can penetrate into a permeable layer of the formation is known as mud filtrate.

Pressure-Volume-Temperature (PVT) properties are an important consideration when developing a formation. In order to accurately model the formation and carry out development operations, reliable PVT properties are invaluable. The impact of an unrepresentative sample can be disastrous. While water based mud filtrate may be benign for collecting hydrocarbon samples, the same thing cannot be said for Oil Based Mud (OBM) filtrate. Because of the high miscibility with the hydrocarbons in the formation, OBM filtrate can alter the PVT behavior of the recovered hydrocarbon sample. Similar distortion effects may be found for other downhole measurements on OBM-contaminated reservoir crude oil. Consequently, it is important to estimate the presence and degree of OBM contamination and, if possible, to correct for it.

SUMMARY OF THE DISCLOSURE

In aspects, the present disclosure is related to methods and apparatuses for estimating a presence of oil-based mud (OBM) in a downhole fluid. Methods may include generating measurement values by measuring a plurality of gross physical properties of the downhole fluid with at least one sensor; and estimating with at least one processor a relative concentration of OBM with respect to the downhole fluid by using a model correlating the measurement values with the relative concentration. The measurement values may include at least one measurement value representative of each gross physical property of the plurality.

Measuring the plurality of gross physical properties may include taking measurements from the downhole fluid in situ. Measuring the plurality of gross physical properties may include estimating the relative concentration in real-time with respect to generating the measurement values. The model may comprise a correlation prediction function mapping the measurement values to the relative concentration. The correlation prediction function may use the measurement values as input to predict the relative concentration. The correlation prediction function may use only the measurement values as input. Methods may include conveying a carrier having the at least one sensor disposed thereon through a borehole penetrating the earth, wherein measuring each of the plurality of gross physical properties is performed downhole.

Aspects of the disclosure may include generating the correlation prediction function by generating a training set by: obtaining a plurality of sample measurement values for a plurality of gross physical properties for each downhole fluid sample of a plurality of downhole fluid samples, each sample measurement value taken from the corresponding downhole fluid sample of the plurality at a specific temperature and a specific pressure both characteristic of a reservoir; generating a plurality of composite independent variables comprising a plurality of variables corresponding to the plurality of gross physical properties of the plurality of downhole fluid samples; and estimating the correlation prediction function by performing a regression on the training set for a dependent variable representing the relative concentration of OBM in terms of the composite independent variables. The sample measurement values may comprise at least one sample measurement value representative of each gross physical property of the plurality, and each downhole fluid sample may have a known relative concentration of OBM. The composite independent variables may comprise terms of a multinomial expansion of variables representing the plurality of physical properties being measured. At least one variable in the multinomial expansion may comprise a reciprocal of a physical property being measured. The regression may comprise a step forward multiple linear regression with substitution. The plurality of gross physical properties may comprise at least one of: i) density, ii) viscosity, iii) sound speed, iv) pressure, and v) temperature as well as variables that can be calculated from these, such as fluid compressibility, which is the reciprocal of the product of fluid density with the square of the fluid sound speed.

General apparatus embodiments may include an instrument configured to generate measurement values, the instrument comprising at least one sensor configured to measure a plurality of gross physical properties of the downhole fluid, wherein the measurement values comprise at least one measurement value representative of each gross physical property of the plurality; and at least one processor configured to estimate a relative concentration of OBM with respect to the downhole fluid by using a model correlating the measurement values with the relative concentration.

Apparatus may further comprise a carrier configured to be conveyed through a borehole penetrating the earth, wherein the at least one sensor is disposed on the carrier and is configured to perform the measuring each of the plurality of gross physical properties downhole. The carrier may comprise a wireline, a drill string, coiled tubing, or a slickline. The apparatus may be configured to measure the plurality of gross physical properties from the downhole fluid in situ. The apparatus may be configured to estimate the relative concentration in real-time with respect to generating the measurement values. The model may comprise a correlation prediction function mapping the measurement values to the relative concentration. The correlation prediction function may be configured to use the measurement values as input to predict the relative concentration. The correlation prediction function may be configured to use only the measurement values as input.

Also disclosed is a method for estimating a chemical composition of hydrocarbons of interest. The method includes: performing a measurement for each physical property of a plurality of physical properties of the hydrocarbons of interest using a sensor to provide a value for each different physical property being measured; and estimating, by a processor, the chemical composition of the hydrocarbons of interest by using a correlation prediction function for each chemical component in the chemical composition in terms of the different physical properties being measured.

Also disclosed is an apparatus for estimating a chemical composition of hydrocarbons of interest. The apparatus includes: a sensor configured to perform a measurement for each physical property in a plurality of physical properties of the hydrocarbons of interest to provide a value for each different physical property being measured; and a processor configured to estimate the chemical composition of the hydrocarbons of interest by using a correlation prediction function for each chemical component in the chemical composition in terms of the different physical properties being measured.

Methods as described above implicitly utilize at least one processor. Some embodiments include a non-transitory computer-readable medium product accessible to the processor and having instructions thereon that, when executed, causes the at least one processor to perform methods described above. Apparatus embodiments may include, in addition to specialized borehole measurement equipment and conveyance apparatus, at least one processor and a computer memory accessible to the at least one processor comprising a computer-readable medium having instructions thereon that, when executed, causes the at least one processor to perform methods described above.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIGS. 5A-5C, collectively referred to as FIG. 5, depict aspects of generating composite independent variables for regression;

FIG. 6 presents one example of ranges of measured physical properties of samples having ranges of known chemical compositions.

DETAILED DESCRIPTION

Figure 1:
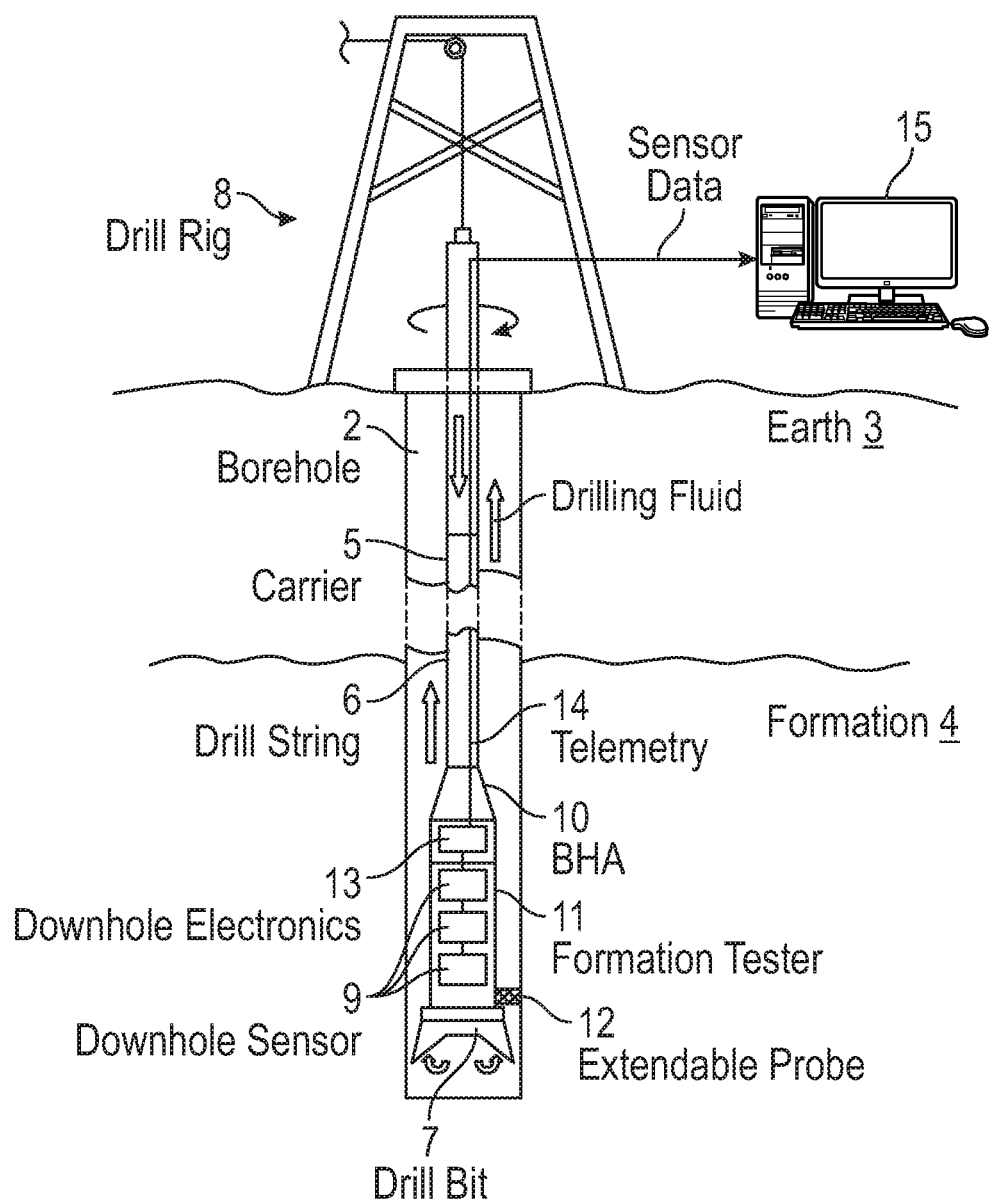
FIG. 1 is a cross-sectional view of an embodiment of a downhole sensor disposed in a borehole penetrating the earth.

Aspects of the present disclosure relate to apparatus and methods for estimating the presence and/or degree of OBM contamination in a downhole fluid. As described above, it is important to estimate the presence and degree of OBM contamination. Ideally, one would mitigate the contamination such that measurements show substantially no effects of contamination. One example of mitigation is to continue pumping fluid from the formation until little or no OBM contamination remains, but doing so would require a real-time estimate of the downhole OBM contamination level while pumping, which aspects of the present disclosure may provide.

OBM contamination may be determined by analysis of chemical composition. Gas chromatography (GC) is the standard surface laboratory method for obtaining detailed chemical composition but retention times are very dependent upon temperature and carrier-gas flow rates and it would be extremely cumbersome to implement GC downhole, which would require a very large and costly engineering effort. Even if one could implement a GC downhole, it would likely take 20 minutes or more to collect a chromatogram out to C20, which is not quite a "real time" measurement. Hence, it would be appreciated in the oil industry if new and efficient methods were developed to estimate OBM contamination in real time.

Previous methods estimated a chemical composition of hydrocarbons such as oil in a downhole environment by spectroscopy. While it is known that a gross physical property of hydrocarbons of interest can be estimated from their chemical composition, it is counter-intuitive to estimate chemical composition of hydrocarbons of interest indirectly from measurements of several physical properties of those hydrocarbons. Conceptually, this method is somewhat analogous to working backwards to determine the individual values of a set of numbers by simply knowing their sum.

For this to be possible, the numbers cannot be random and uncorrelated to each other but the numbers must have some relationship to each other such as a constraint equation on their relative concentrations. Indeed, a crude oil is not a random mixture of various saturates, aromatics, resins, and asphaltenes but a delicate balance of all of its components. Therefore, the amount of one component in a crude oil is related in complex, and often unknown, ways to the amounts of the other components in that crude oil. Otherwise, the mixture of compounds in the crude oil would not stay in solution over long periods of time For example, the polarity of components of crude oil range from completely nonpolar saturates to highly polar asphaltenes. Like dissolves like so polar and nonpolar compounds will not go into solution together unless there is a continuum of all intermediate polarity compounds to hold them together. Compounds from each range of polarity hold on to other compounds that have slightly higher and slightly lower polarity so as to bridge the large polarity gap. It is known that from C10 to C29, we expect the log of the concentration of each compound versus carbon number to follow a downward sloping straight line. The deviations of C15-C19 above this straight trend line is integrated, which is the standard way that OBM contamination in crude oil is currently measured by gas chromatography in a surface lab.

The correlation method of this disclosure is indirectly making use of the inherent natural correlations between chemical components in a crude oil. As disclosed herein, by using measured values of several different physical properties, a process of working backwards from gross physical properties can be used to estimate corresponding detailed chemical composition of crude oils. This process can provide a synthetic chromatograph from values of physical properties of a hydrocarbon of interest.

The solution to this problem is based upon measuring gross physical properties of a large number of samples of hydrocarbons at reservoir temperatures and pressures along with measuring their chemical compositions so as to create a training set. The weight percentages of detailed chemical composition (C1, C2, etc.) become the dependent variables in the subsequent regressions on the training set. Various composite independent variables are generated from the different types of physical properties. For simplicity of discussion, the term "gross physical properties" is intended to include the thermodynamic state variables—temperature and pressure. A regression of detailed chemical composition in terms of the various composite independent variables is performed to provide a statistically significant correlation and prediction function. Consequently, by measuring physical properties of hydrocarbons of interest downhole, the chemical composition of those chemical properties can be estimated using the correlation prediction function.

In the present application, however, rather than determine chemical composition of methane (C1), ethane (C2), and so on as in the previous patent application, the filtrate contamination by OBM, often C16-C18 or, perhaps, as broad as C15-C19, is estimated. Aspects of the present disclosure may include methods for estimating a presence of oil-based mud (OBM) in a downhole fluid. Methods may include generating measurement values by measuring a plurality of gross physical properties of the downhole fluid with at least one sensor; and estimating with at least one processor a relative concentration of OBM with respect to the downhole fluid by using a model correlating the measurement values with the relative concentration. The measurement values may comprise at least one measurement value representative of each gross physical property of the plurality. Measuring the plurality of gross physical properties may include taking measurements from the downhole fluid in situ. Methods may include estimating the relative concentration in real-time with respect to generating the measurement values.

The model may comprise a correlation prediction function mapping the measurement values to the relative concentration. The correlation prediction function may use the measurement values as input to predict the relative concentration. The correlation prediction function may use only the measurement values as input, so as to estimate the presence of OBM directly from the correlation of gross physical properties. In some embodiments, the correlation prediction function may use the measurement values as input, along with other downhole parameters. For example, the estimation of OBM concentration may include using a model mapping the measurement values and one or more hydrocarbon values (e.g., C1-C7) to the relative concentrations. The hydrocarbon values may be estimated using the technique herein or any other technique. Alternatively, or additionally, estimation may include using a model mapping the measurement values to the relative concentrations of one or more hydrocarbon molecules representative of the mud (e.g., C16-C18), either alone or in combination with other hydrocarbon molecules.

Estimating OBM contamination using techniques in accordance with the present disclosure is simpler and easier to implement than techniques of the prior art because it employs a prediction model for relative concentration of OBM based upon the sample's gross physical properties such as temperature, pressure, density, viscosity, sound speed or compressibility (all of which can be measured within a few seconds) instead of directly measuring concentrations. As such, no optical absorption or mixing rules are needed. Endpoint estimation of pure crude or pure mud filtrate is unnecessary, and knowing aromatic, saturate, resin or asphaltene fractions or iterative processes are not required. Further, it may be carried out while pumping, such as, for example, using the Reservoir Characterization Instrument™ service provided commercially by Baker Hughes, a G.E. company, LLC.

The techniques of the present disclosure have a particular advantage with respect to traditional chromatographic techniques of determining chemical composition and the extent of OBM contamination. A chromatogram separates components of a mixture by the retention time that it takes for each compound to pass through a given length (e.g., approximately 50 meters) of chromatographic capillary column. Generally, the lighter compounds such as C1 (methane), C2 (ethane), C3 (propane) come out first, in order by molecular weight, and then the heavier compounds come out. As oil-based muds are usually in the range of C15-C19, they exit the column much later, resulting in delayed (non-real time) responses. Measuring the OBM contamination percentage at a surface laboratory necessitates the use of methods utilizing variations (local peaks above a trend line) from a log linear plot of component concentration over some carbon number range, or similar techniques.

FIG. 1 is a cross-sectional view of an embodiment of a bottomhole assembly (BHA) 10 disposed in a borehole 2 penetrating the earth 3 having a formation 4. A carrier 5 is configured to convey the BHA 10 through the borehole 2. In one or more embodiments, the carrier 5 is a drill string 6 in a logging-while-drilling (LWD) embodiment. Alternatively, the carrier 5 can be an armored wireline in an embodiment referred to as wireline logging. Coupled to the distal end of the drill string 6 is a drill bit 7 configured to cut or disintegrate rock to form the borehole 2. A drill rig 8 is configured to conduct drilling operations such as rotating the drill string 6 and thus the drill bit 7 in order to drill the borehole 2. In addition, the drill rig 8 may be configured to pump drilling fluid (mud) through the drill string 6 in order to flush cuttings from the borehole 2 and lubricate the drill bit 7.

Disposed in the BHA 10 is a formation tester 11. The formation tester 11 is configured to extract a sample of formation fluid, such as hydrocarbons of interest, through a wall of the borehole 2 using an extendable probe 12. One or more sensors 9 are configured to sense multiple physical properties of the fluid sample downhole. Non-limiting embodiments of the gross physical properties include density, viscosity, sound speed, pressure, temperature, and compressibility. A single physical property may be sensed by one sensor 9 or multiple physical properties may be sensed by one sensor 9. Sensor data may be processed downhole by downhole electronics 13. Alternatively, sensor data may be transmitted to the surface of the earth using telemetry 14 and received for processing by a surface computer processing system 15. In addition, sensor data processing functions may be performed by a combination of the downhole electronics 13 and the surface computer processing system 15. Non-limiting embodiments of the telemetry include wired drill pipe and pulsed-mud telemetry. A depth at which the fluid sample is extracted may be recorded in order to correlate the sensed physical properties with the depth at which the corresponding sample was extracted. Accordingly, the chemical composition may be determined as a function of depth. It can be appreciated that sensor data can be processed as soon as it is received and thus provide answers to a user in real-time. Myriad sensors for providing measurements of gross physical properties are available. See for example, U.S. Pat. Nos. 5,622,223; 5,741,962; 5,377,755 to Michaels et al; U.S. Pat. No. 6,609,568 to Krueger et al.; U.S. Pat. No. 7,219,541 to DiFoggio; U.S. Pat. No. 8,037,747 to DiFoggio; and U.S. patent application publication Serial No. US 2015/0057935 to Wu; each of which is incorporated herein by reference in its entirety.

Figure 2:
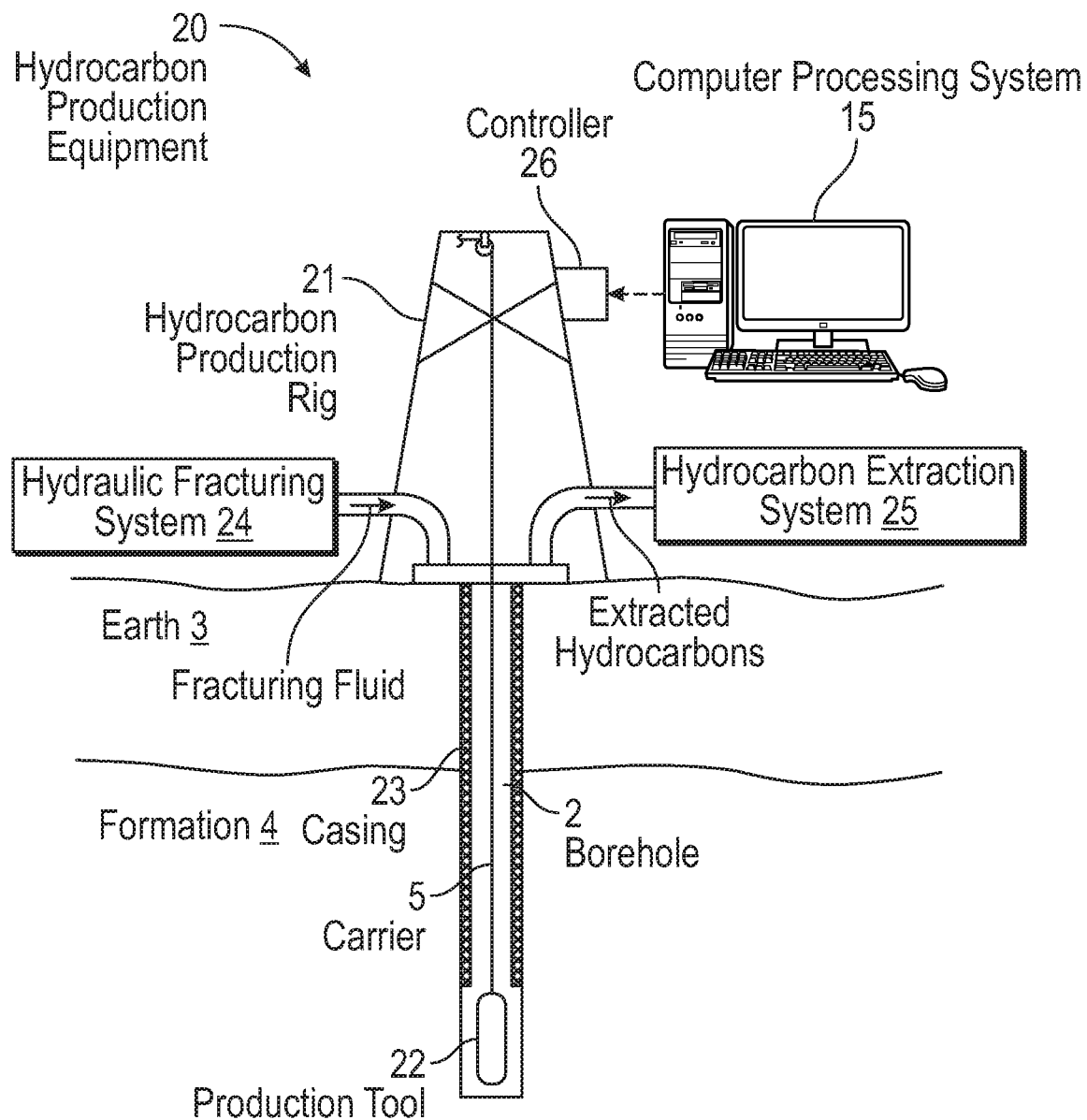
FIG. 2 is a cross-sectional view of an embodiment of hydrocarbon production equipment.

FIG. 2 is a cross-sectional view of an embodiment of hydrocarbon production equipment 20 that is configured to perform hydrocarbon production actions based upon at least one target parameter ('parameter of interest') selected from the chemical composition of the hydrocarbons of interest or the relative concentration of OBM. As the chemical composition may be presented as a function of depth, this information may be used to determine a depth at which certain hydrocarbon production actions are performed. The hydrocarbon production equipment 20 may include a hydrocarbon production rig 21 configured to conduct hydrocarbon production actions such as lowering or raising a production tool 22 in the borehole 2. In one or more embodiments, the production tool 22 is configured to perforate a casing 23 lining the borehole 2 at a selected depth or range of depths. The hydrocarbon production equipment 20 may also include a hydraulic fracturing system 24 configured to hydraulically fracture the formation 4 in a selected depth interval. The hydrocarbon production equipment 20 may also include a hydrocarbon extraction system 25 configured to pump and process hydrocarbons from the formation 4. The chemical composition of the hydrocarbons of interest can give an indication as to the state of the hydrocarbons of interest once at the surface (at atmospheric temperature and pressure) so that they can be processed appropriately. The hydrocarbon extraction system 25 may include pumps, valves and storage facilities (all not shown) appropriate for the chemical composition of the hydrocarbons of interest being extracted. For example, a hydrocarbon extraction system for a chemical composition indicating predominantly oil may be different from a hydrocarbon extraction system for a chemical composition indicating predominantly gas. Similarly, a hydrocarbon extraction system for light oil may be different from a hydrocarbon extraction system for heavy oil. A controller 26 may be used to control the hydrocarbon production functions and/or configurations and may receive input based on the estimated hydrocarbon chemical composition and optional corresponding depth from the surface processing system 15.

Figure 3A:
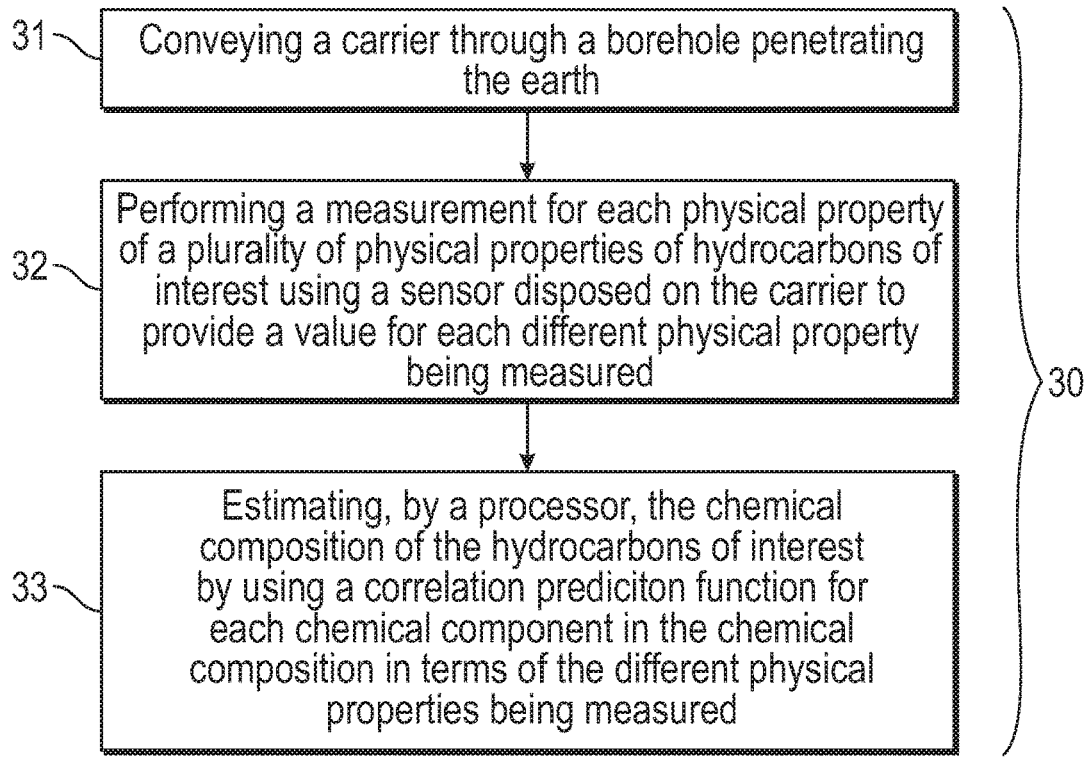
FIG. 3a depicts a flow chart illustrating a method for estimating a chemical composition of hydrocarbons of interest.

FIG. 3a depicts a flow chart illustrating a method 30a for estimating a chemical composition of hydrocarbons of interest. Block 31a calls for conveying a carrier through a borehole penetrating the earth. Non-limiting embodiments of the carrier include a wireline, a drill string, coiled tubing, and a slick line.

Block 32a calls for performing a measurement for each physical property of a plurality of physical properties of hydrocarbons of interest using a sensor disposed on the carrier to provide a value for each different physical property being measured. Non-limiting embodiments of the physical properties being sensed and measured include density, viscosity, sound speed, temperature, pressure, and compressibility. The sensor can represent a single sensor for each physical property sensed. Alternatively, a single sensor can sense two or more of the physical properties, such as the tuning fork sensor, which can measure both density and viscosity.

Block 33a calls for estimating, by a processor, the chemical composition of the hydrocarbons of interest by using a correlation prediction function for each chemical component in the chemical composition in terms of the different physical properties being measured. In one or more embodiments, the correlation prediction function is a mathematical equation for each chemical component in the chemical composition such that a concentration of the chemical component in the chemical composition can be predicted by entering the values of the measured physical properties. For example, the concentrations of methane (C1), ethane (C2), propane (C3), butane (C4), pentane (C5), hexane (C6), and heptane (C7) may be estimated by inputting the values of measured physical properties, a, b, c, d, e, and f into the following correlation prediction functions, f1, f2, f3, f4, f5, f6, and f7:

$$C1=f1(a,b,c,d,e,f)$$

$$C2=f2(a,b,c,d,e,f)$$

$$C3=f3(a,b,c,d,e,f)$$

$$C4=f4(a,b,c,d,e,f)$$

$$C5=f5(a,b,c,d,e,f)$$

$$C6=f6(a,b,c,d,e,f)$$

$$C7=f7(a,b,c,d,e,f)$$

In one or more embodiments, carbon chains greater than C7 may be grouped together with C7 and simply referred to as C7+. Alternatively, carbon chains up to C18 may be estimated, or selected examples of these may be estimated, such as C11-C20, C16-C18, and so on.

Figure 7A:
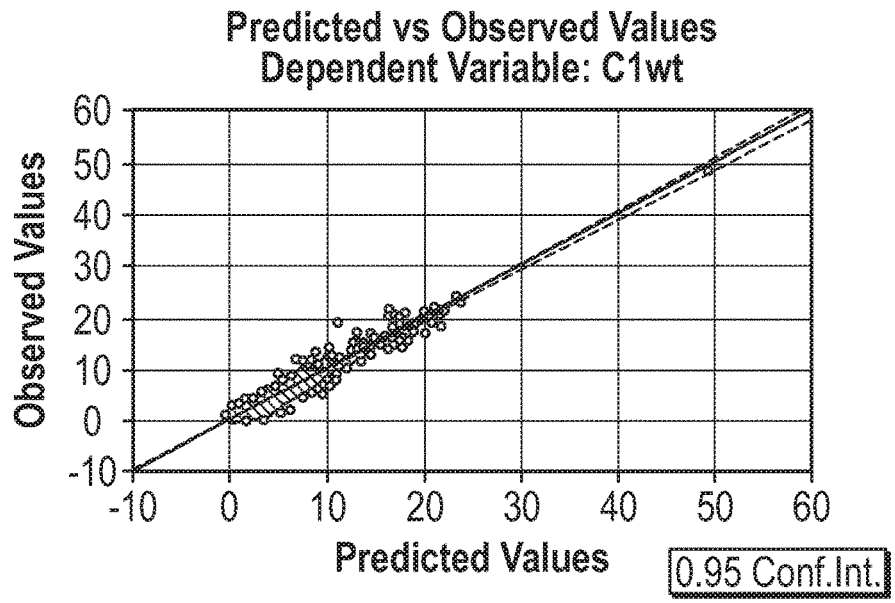
FIGS. 7A-7G depict aspects of observed values versus predicted values for chemical components in a chemical composition of a hydrocarbon of interest.
Figure 7B:
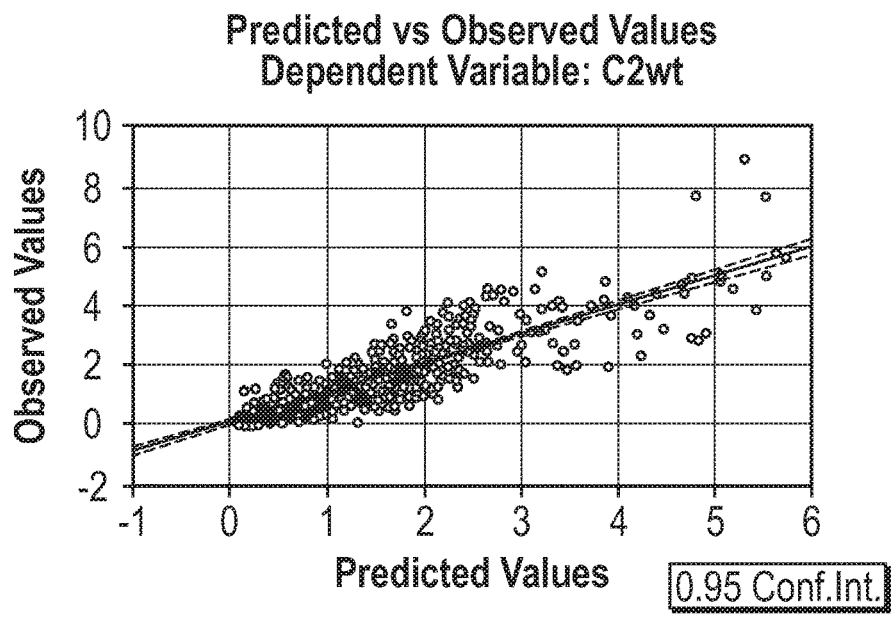
Figure 7C:
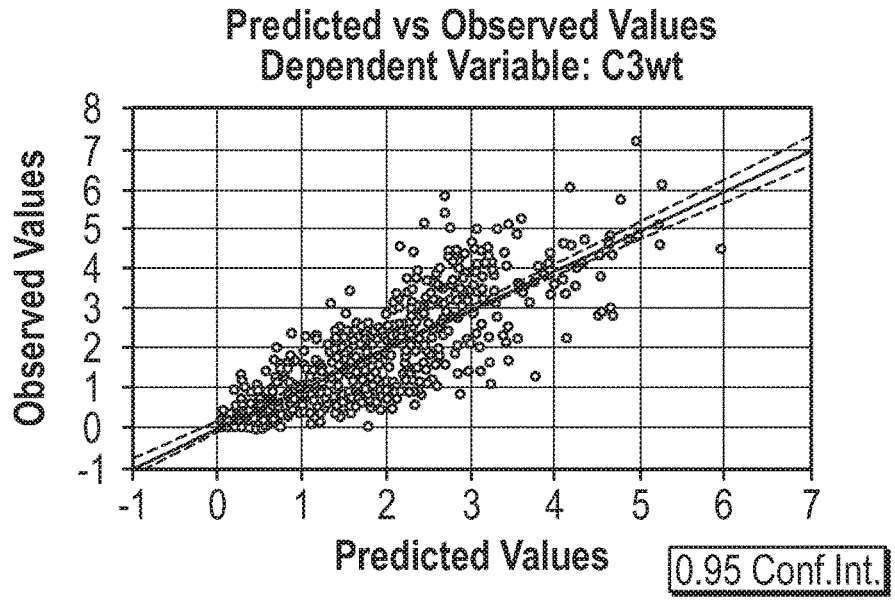
Figure 7D:
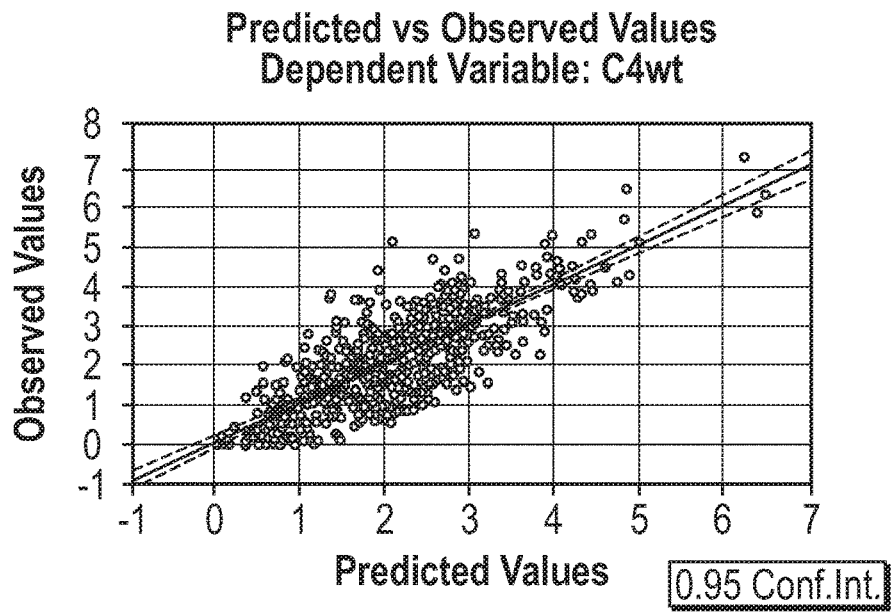
Figure 7E:
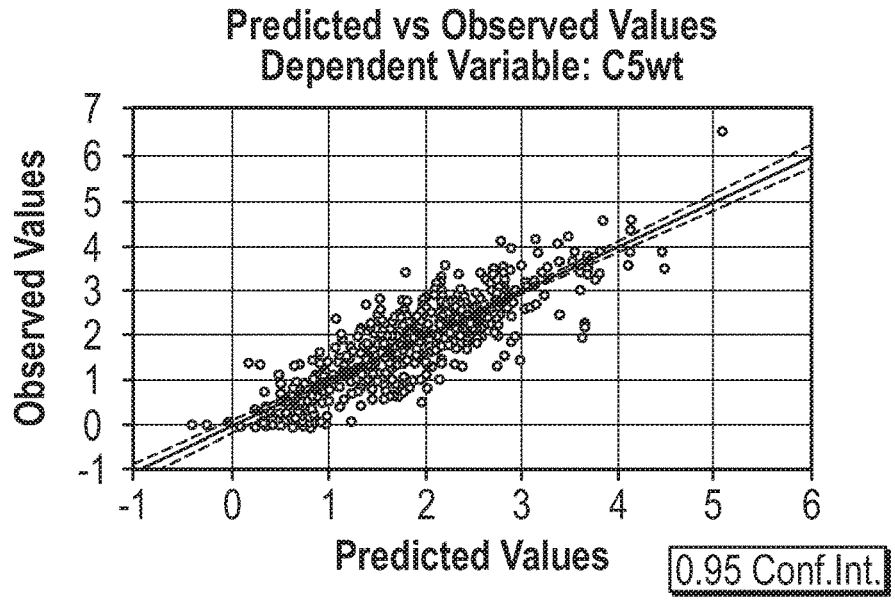
Figure 7F:
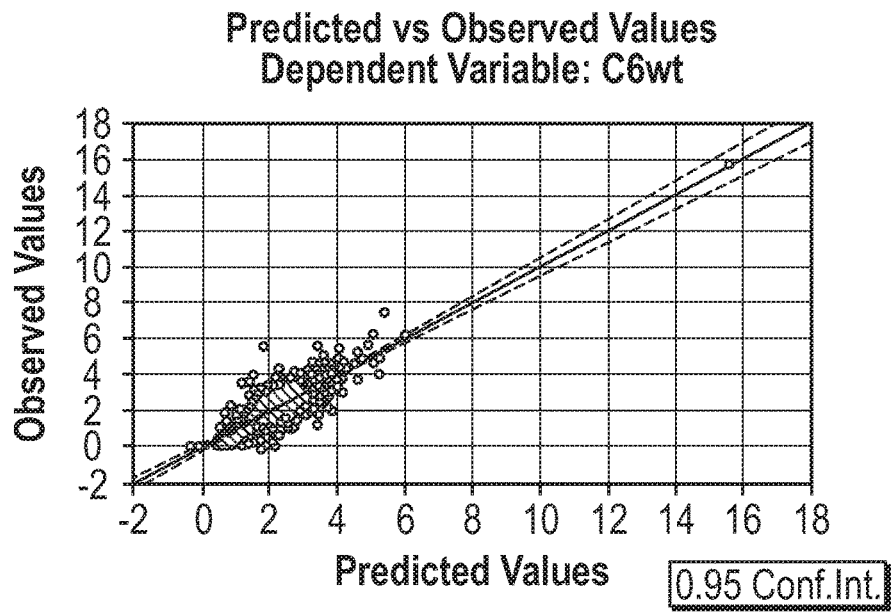
Figure 7G:
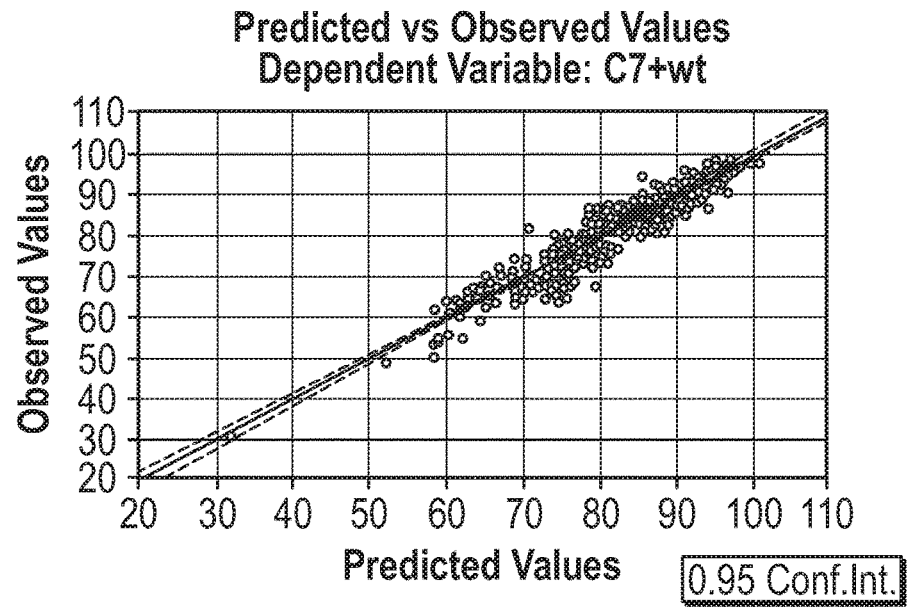

For example, for the methane weight percentage, C1wt, the single most correlating composite independent variable for a set of approximately 500 live crude oils is the reciprocal of the product of temperature (° K) with density squared (g/cc) yielding the correlation prediction function, $C1wt=-9.80587598+2955.4188/(D^2T)$ but the fraction of data explained by this correlation ($R^2$) is only 0.728 and the standard error of calibration (SEC) is 2.700 in the prediction of weight percent. The next most correlating variable that the regression software (Statistica) added during step forward regression was the pressure (kpsi) yielding the equation, $C1wt=-10.4650253+2544.13363/(D^2T)+0.700564866$ P, which has an $R^2=0.858$ with an SEC=1.954. Continuing on, subject to the requirement that all independent variables in the model have a statistical probability of less than 5% that its corresponding regression coefficient might actually be zero, an $R^2=0.929$ and SEC=1.392 are obtained as shown in FIG. 7A using ten composite independent variables. Similarly, FIGS. 7B-7G show regression results for predicted versus observed values for C2wt, C3wt, C4wt, C5wt, C6wt, and C7+wt percentages.

Figure 7H:
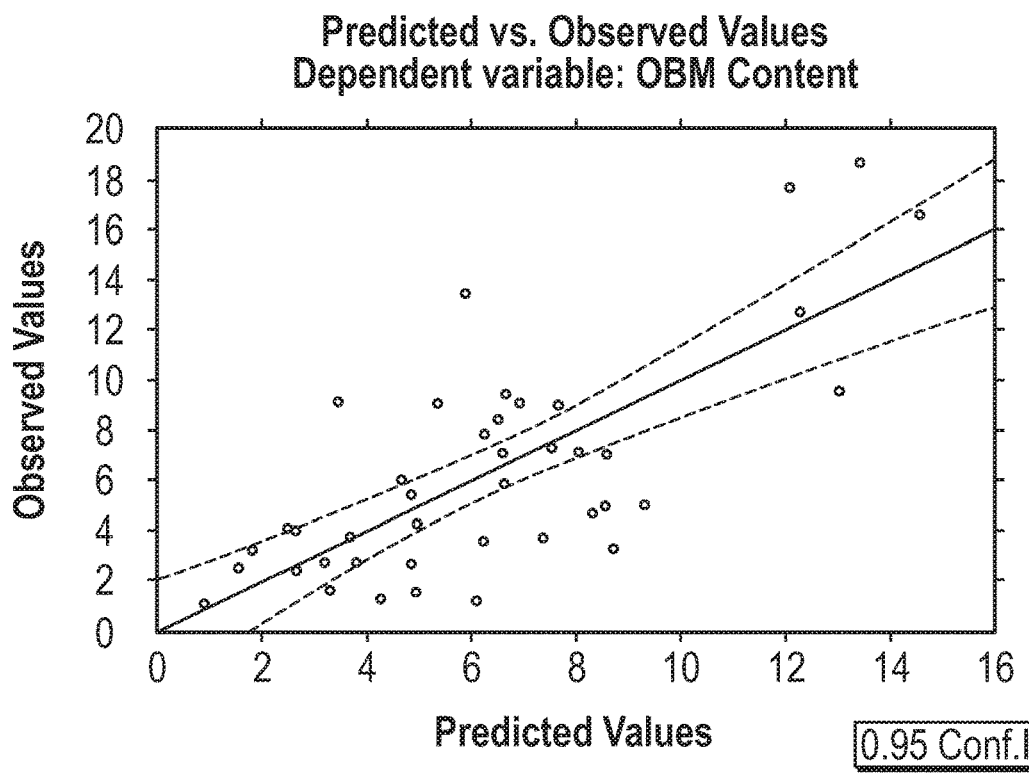
FIG. 7H shows regression results for predicted versus observed values of OBM contamination percentages using eight composite variables.

Similarly, FIG. 7H shows regression results for predicted versus observed values of OBM contamination percentages using eight composite variables, which are based only on pressure, temperature, and density, wherein $R^2=0.548$ and SEC=3.361. This OBM calibration set had far fewer samples than the earlier C1-C7 calibration set. With a larger OBM calibration set, more fitting variables could have been used without the risk of overfitting and, perhaps, an even better correlation would have been obtained.

These plots are not all at the same scale so, for enlarged-scale plots that cover a smaller range, the correlations do not visually appear as good as for plots covering a much larger range even when the SEC is actually lower (better). Not shown are some good regressions for isobutane and normal butane where iC4wt+nC4wt=C4wt (i=iso and n=normal) and for isopentane and normal pentane where iC5wt+nC5wt=C5wt. Although the above discussion describes step-forward multiple linear regression, other linear regression methods can be used such as Principal Components Regression (PCR) or Partial Least Square regression (PLS). Other modeling methods, such as Neural Networks (NN), which can create linear or nonlinear models, could also be used. Note that, if there is random error, $\sigma_L$, in the laboratory values for the C1, C2, C3, ... C7+ values used in the training set, then the model's Standard Error of Calibration will include both that lab imprecision, $\sigma_L$, as well as any modeling error, $\sigma_M$, so that the apparent total $SEC^2 = Sqrt(\sigma_L^2 + \sigma_M^2)$. Linear least squares models fit a hyperplane to a set of data points in hyperspace so that the sum of the squares of the distances of points above the hyperplane to it will equal the sum of the squares of the distances of points below the hyperplane to it.

Therefore, the hyperplane model acts to average out random lab error in the training set calibration values, which means that the model's actual prediction performance on unknown samples can be better than the regression's SEC (See R. DiFoggio, *Examination of Some Misconceptions about Near-Infrared Analysis*, Applied Spectroscopy January 1995 49: 67-75, doi:10.1366/0003702953963247). Block 33 may also include inputting the measured values of the different physical properties into the correlation prediction function and obtaining as output the chemical composition of the hydrocarbon sample being evaluated, which may then be processed to arrive at relative concentration of OBM. The output may then be transmitted as a signal to a user for performing further actions dependent upon the chemical composition and/or relative concentration of OBM.

Figure 3B:
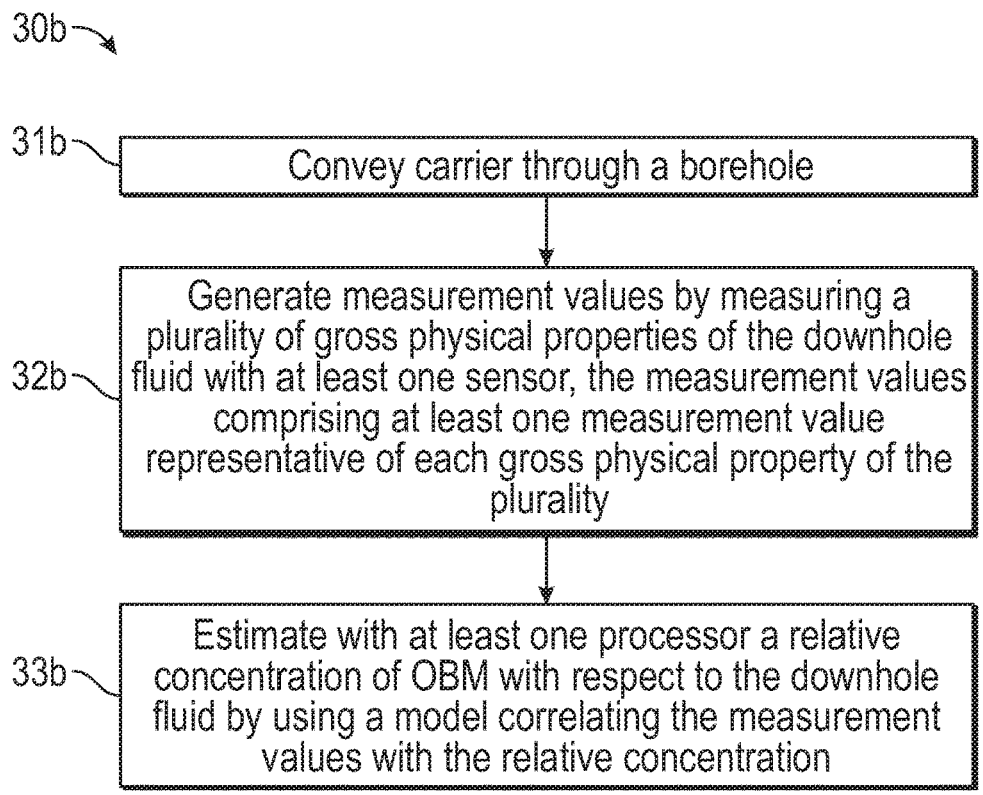
FIG. 3b depicts a flow chart illustrating a method for estimating relative concentration of OBM in a downhole fluid in accordance with embodiments of the present disclosure.

FIG. 3b depicts a flow chart illustrating a method 30b for estimating relative concentration of OBM in a downhole fluid in accordance with embodiments of the present disclosure. Block 31b comprises conveying a carrier through a borehole penetrating the earth. Non-limiting embodiments of the carrier include a wireline, a drill string, coiled tubing, and a slick line. Block 32b is carried out by generating measurement values by measuring a plurality of gross physical properties of the downhole fluid with at least one sensor, the measurement values comprising at least one measurement value representative of each gross physical property of the plurality. Measuring the plurality of gross physical properties may include taking measurements from the downhole fluid in situ.

Block 33b is carried out by estimating with at least one processor a relative concentration of OBM with respect to the downhole fluid by using a model correlating the measurement values with the relative concentration. Estimating the relative concentration may be carried out in real-time with respect to generating the measurement values. The model may comprise a correlation prediction function mapping the measurement values to the relative concentration. The correlation prediction function may use the measurement values as input to predict the relative concentration.

Figure 4A:
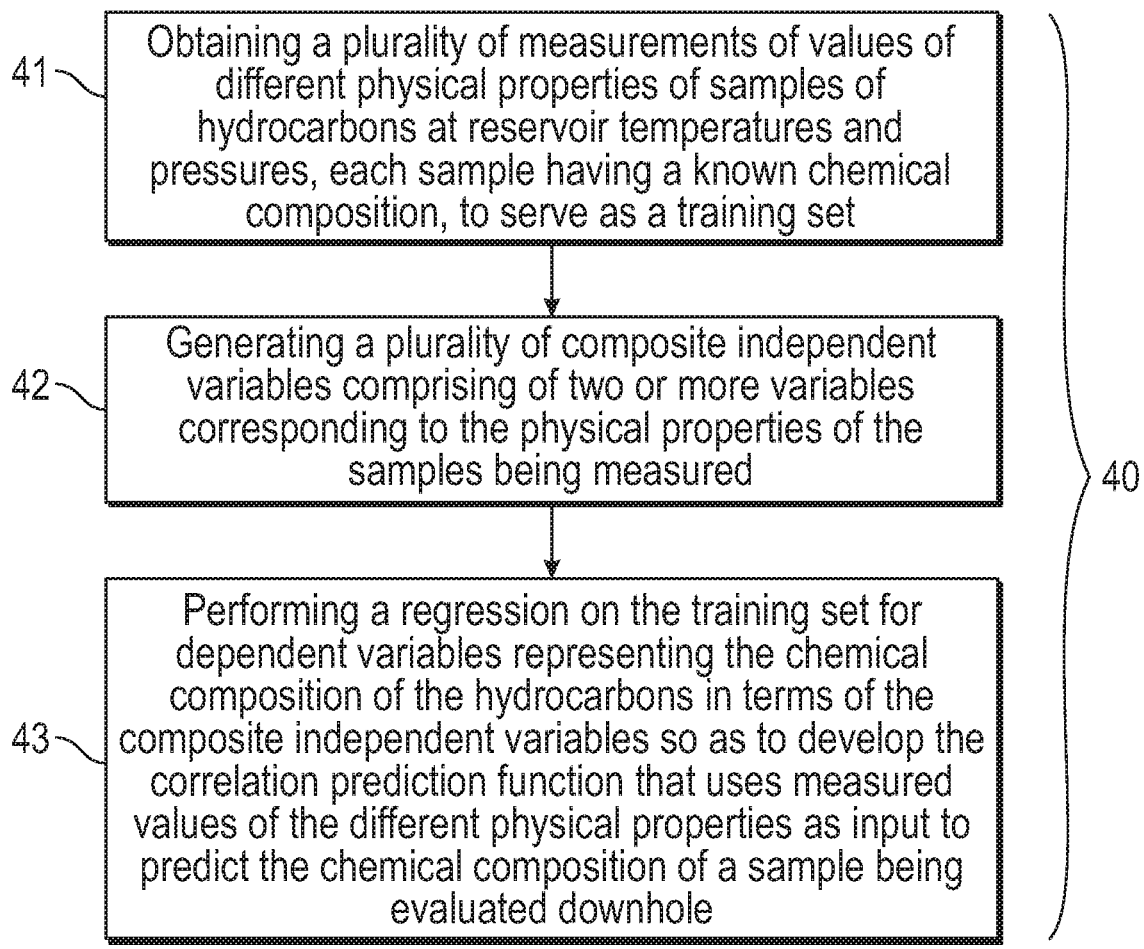
FIG. 4a depicts a flow chart illustrating a method 40a for generating a correlation prediction function that correlates measured physical properties to a chemical composition.

FIG. 4a depicts a flow chart illustrating a method 40a for generating a correlation prediction function that correlates measured physical properties to a chemical composition. Block 41a calls for obtaining a plurality of measurements of values of different physical properties of samples of hydrocarbons at reservoir temperatures and pressures, each sample having a known chemical composition, to serve as a training set. To be clear, the training set has measured values of physical properties of multiple samples of different hydrocarbons at in-situ temperatures and pressures, each sample having a measured chemical composition. The different physical properties are those physical properties used in the correlation prediction function discussed above. This block may also include performing the plurality of measurements using at least one sensor. FIG. 6 presents one example of ranges of measured physical properties of samples having ranges of known chemical compositions.

Block 42a calls for generating a plurality of composite independent variables comprising two or more variables corresponding to the physical properties of the samples being measured. That is, each composite independent variable includes two or more variables with each variable representing a different physical property. For example, composite independent variable 1 (CIV1) may represent $(a^x \cdot b^y)$ for physical property variables a and b. Composite independent variable 2 (CIV2) may represent $(a^x/b^y)$. With more physical property values and many choices for exponents, there can be many types of combinations and permutations resulting in a large number of composite independent variables such as in the hundreds or even more.

FIG. 5 illustrates one example of how to generate an expanded set of linearly-independent composite independent variables from an original set of four independent variables, Density (D), Viscosity (V), Pressure (P), and Temperature (T). Of course, an even larger original set of independent variables could be used, which also included Compressibility (C) and Sound Speed (SS), but that would have made this example more complex for teaching purposes. This example of a process is similar to individual product terms of a multinomial expansion in which the sum of the exponents of each term is equal to the power to which the multinomial is taken. For the example below, shown as "Third Order" in FIG. 5C, the multinomial power is 3 and the sum of the exponents in each term is also 3:

$$(D+V+P+T)^3 = 1D^3V^0P^0T^0 + 3D^2V^1P^0T^0 + 3D^2V^0P^0T^1 +$$
$$3D^1V^2P^0T^0 + 6D^1V^1P^1T^0 + 6D^1V^1P^0T^1 +$$
$$3D^1V^0P^2T^0 + 6D^1V^0P^1T^1 + 3D^1V^0P^0T^2 +$$
$$1D^0V^3P^0T^0 + 3D^0V^2P^1T^0 30\ 3D^0V^2P^0T^1 +$$
$$3D^0V^1P^2T^0 + 6D^0V^1P^1T^1 + 3V^1P^0T^2 + 1D^0V^0P^3T^0 +$$
$$3D^0V^0P^2T^1 + 3D^0V^0P^1T^2 + 1D^0V^0P^0T^3$$

In FIG. 5A ("First Order") the multinomial power is one, while in FIG. 5B ("Second Order") the multinomial power is two. To further expand the list of linearly-independent composite variables, D could be replaced by its reciprocal 1/D in each term. Alternatively, V could be replaced by its reciprocal or P by its reciprocal or T by its reciprocal. Next, any two of the original variables, D, V, P, and T could be replaced by their reciprocals. Next, any combination of three variables or all four variables could be replaced by their reciprocals. Similarly, fractional power replacements for variables such as square roots could also be used. Logarithms may also be used. A simple way to exhaustively prepare a list of all n-order terms of an m-term multinomial taken to the n-th power is to count in the number base, (n+1), from 1 to $(n+1)^m - 1$ and then to retain only those sets of digits for which digit sum is n, which can easily be done in a spreadsheet. Note that the composite independent variables created in this way will also be linearly independent of one another, which is important when performing multiple linear regression so that there will be no linear redundancy in the set of independent variables.

Referring back to FIG. 4a, Block 43a calls for performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole. Downhole evaluation relates to obtaining a hydrocarbon sample downhole and performing measurements downhole of different physical properties under in-situ conditions of temperature and pressure to obtain values of the different physical properties. "Regression" relates to estimating a mathematical relationship (i.e., correlation function) between the chemical composition of the hydrocarbons of interest and the composite independent variables using the training set. Different types of regression analysis techniques may be used. In one or more embodiments, a step forward Multiple Linear Regression (MLR) with substitution is used. In this technique, the choice or predictive composite variables is carried out by an automatic procedure such as an algorithm first proposed by Efroymson in 1960. This procedure generally takes the form of a sequence of F-tests or t-tests, but other techniques are possible, such as adjusted $R^2$ in order to select the composite variables providing the best fit. The step forward multiple linear regression involves starting with no variables in the model, testing the addition of each variable using a chosen model fit criterion, adding the variable (if any) whose inclusion gives the most statistically significant improvement of the fit, and repeating this process until none improves the model to a statistically significant extent. Another type of regression analysis is backward elimination, which involves starting with all candidate variables, testing the deletion of each variable using a chosen model fit criterion, deleting the variable (if any) whose loss gives the most statistically insignificant deterioration of the model fit, and repeating this process until no further variables can be deleted without a statistically significant loss of fit. Yet another, type of regression analysis is bidirectional elimination, a combination of the above, testing at each step for variables to be included or excluded. Commercial software, such as Statistica (previously sold by StatSoft of Tulsa, Okla. and, after its acquisition, by TIBCO Software Inc. of Palo Alto, Calif.) is readily available to perform such regression analysis techniques.

Note that "with substitution" can be significant because, in step forward multiple linear regression, the algorithm starts out with the highest correlating independent variable and then seeks a second independent variable that provides the most complementary information to the first. However, upon picking a third independent variable, that third variable, together with the second, may model the data so well that the first variable becomes statistically insignificant, in which case the first variable is dropped. Specifically, the user sets two F-test thresholds, one for entering a new independent variable into the model and another for removing a current independent variable from the model. This situation can occur when the second and third independent variables are not individually highly correlated to the dependent variable but they provide highly complementary information so that, together, they provide better correlation than the first variable alone so that inclusion of the first variable in a three-variable model becomes statistically insignificant and the first variable is then dropped from the model.

Figure 4B:
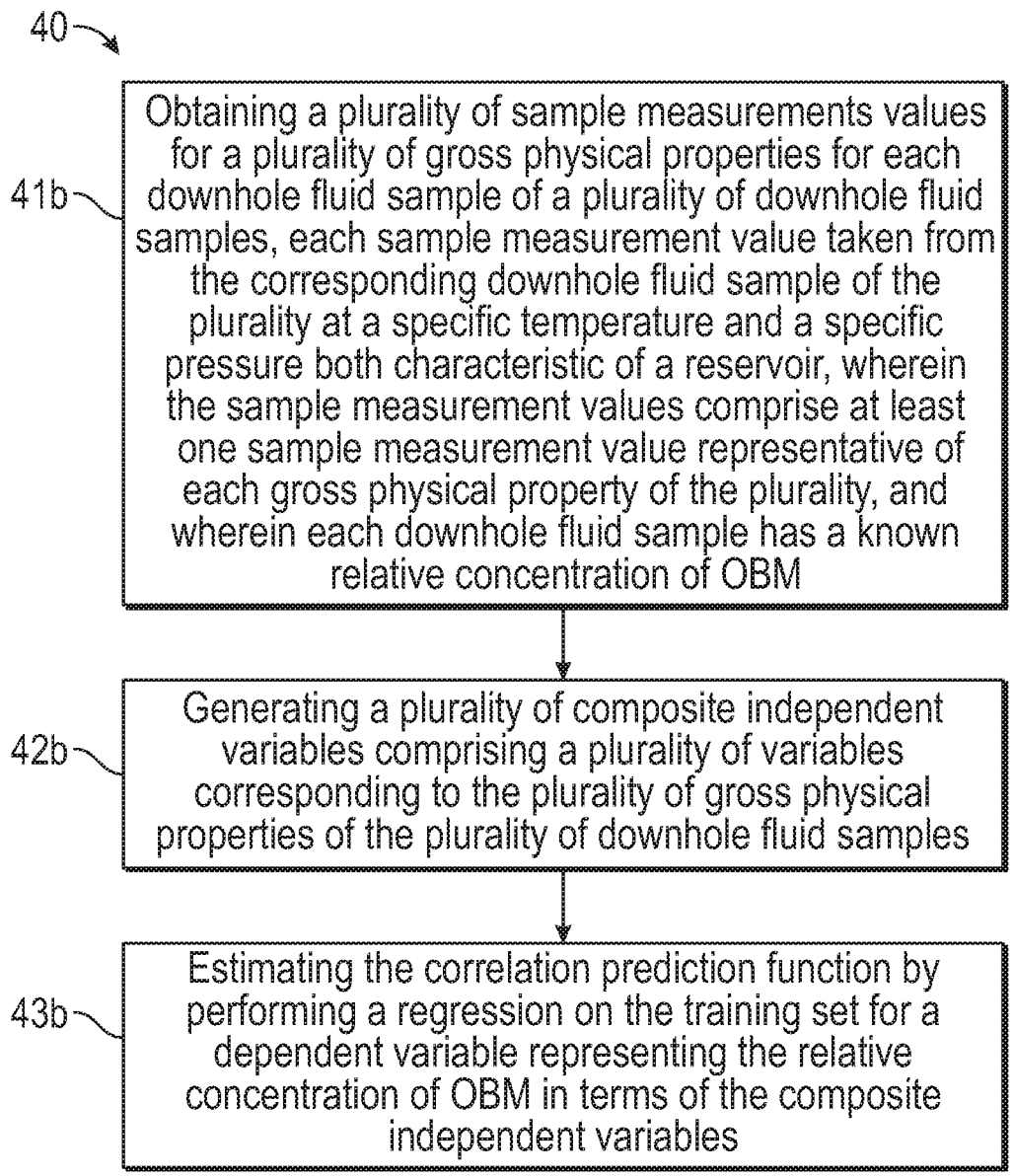
FIG. 4b depicts a flow chart illustrating methods for generating a correlation prediction function in accordance with embodiments of the present disclosure.

FIG. 4b depicts a flow chart illustrating methods for generating a correlation prediction function in accordance with embodiments of the present disclosure. Block 41b may be carried out by obtaining a plurality of sample measurement values for a plurality of gross physical properties for each downhole fluid sample of a plurality of downhole fluid samples, each sample measurement value taken from the corresponding downhole fluid sample of the plurality at a specific temperature and a specific pressure both characteristic of a reservoir, wherein the sample measurement values comprise at least one sample measurement value representative of each gross physical property of the plurality, and wherein each downhole fluid sample has a known relative concentration of OBM.

Block 42b may be carried out by generating a plurality of composite independent variables comprising a plurality of variables corresponding to the plurality of gross physical properties of the plurality of downhole fluid samples. Block 43b may be carried out by estimating the correlation prediction function by performing a regression on the training set for a dependent variable representing the relative concentration of OBM in terms of the composite independent variables. Block 42b and block 43b may be carried out using the techniques as described above with reference to blocks 42a and 43a, respectively.

The methods and apparatuses disclosed herein provide several advantages. One advantage is that the physical properties required for being input into the correlation function are readily measurable downhole and avoid the expense and time necessary to transfer a sample from the formation to a surface laboratory under in-situ conditions. Another advantage is that because the physical properties can be readily measured downhole, the methods disclosed herein can be implemented in real time instead of waiting months for a surface laboratory analysis. By receiving hydrocarbon chemical composition information in real time, petroleum analysts and engineers can quickly implement or alter completion procedures and/or configure hydrocarbon production equipment based on the chemical composition. Real time analysis of crude oil composition allows the operator to make much earlier ordering decisions for the specific types of expensive and long lead time production and processing equipment that will be needed.

Yet another advantage is that reservoir connectivity can be determined based on the chemical composition of layers being the same or different. Reservoir connectivity determination can be useful in planning and executing plans for borehole or reservoir completion. Disconnected reservoirs will need separate wells to drain them, which can be a very expensive undertaking, especially offshore.

Set forth below are some embodiments of the foregoing disclosure:

Embodiment 1: A method for estimating a chemical composition of hydrocarbons of interest, the method comprising: performing a measurement for each physical property of a plurality of physical properties of the hydrocarbons of interest using a sensor to provide a value for each different physical property being measured; and estimating, by a processor, the chemical composition of the hydrocarbons of interest by using a correlation prediction function for each chemical component in the chemical composition in terms of the different physical properties being measured.

Embodiment 2: The method according to any prior embodiment, further comprising generating the prediction function by: obtaining a plurality of measurements of values of different physical properties of samples of hydrocarbons at reservoir temperatures and pressures, each sample having a known chemical composition, to serve as a training set; generating a plurality of composite independent variables comprising one or more variables corresponding to the physical properties of the samples being measured; and performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole.

Embodiment 3: The method according to any prior embodiment, wherein the chemical composition comprises a relative concentration for each of two or more carbon molecules.

Embodiment 4: The method according to any prior embodiment, wherein the two or more carbon molecules comprises methane (C1), ethane (C2), propane (C3), butane (C4), pentane (C5), hexane (C6), and heptanes and higher (C7+).

Embodiment 5: The method according to any prior embodiment, wherein the prediction function comprises a prediction function for each of the two or more carbon molecules.

Embodiment 6: The method according to any prior embodiment, wherein the composite independent variables comprise terms of a multinomial expansion of variables representing the plurality of physical properties being measured.

Embodiment 7: The method according to any prior embodiment, wherein at least one variable in the multinomial expansion is a reciprocal of a physical property being measured.

Embodiment 8: The method according to any prior embodiment, wherein the regression comprises a step forward multiple linear regression with substitution.

Embodiment 9: The method according to any prior embodiment, wherein the plurality of physical properties comprises at least one selection from a group consisting of density, viscosity, sound speed, pressure, and temperature.

Embodiment 10: The method according to any prior embodiment, wherein the estimating is performed in real time upon receiving the measurements for each physical property in the plurality of physical properties of the hydrocarbons of interest.

Embodiment 11: The method according to any prior embodiment, further comprising performing a hydrocarbon production action using the estimated chemical composition of the hydrocarbons of interest.

Embodiment 12: The method according to any prior embodiment, wherein the hydrocarbon production action comprises hydraulic fracturing an earth formation containing the hydrocarbons in a selected range of depths.

Embodiment 13: The method according to any prior embodiment, further comprising conveying a carrier through a borehole penetrating the earth, wherein the sensor is disposed on the carrier and the measurement for each physical property is performed downhole.

Embodiment 14: An apparatus for estimating a chemical composition of hydrocarbons of interest, the apparatus comprising: a sensor configured to perform a measurement for each physical property in a plurality of physical properties of the hydrocarbons of interest to provide a value for each different physical property being measured; and a processor configured to estimate the chemical composition of the hydrocarbons of interest by using a correlation prediction function for each chemical component in the chemical composition in terms of the different physical properties being measured.

Embodiment 15: The apparatus according to any prior embodiment, further comprising a carrier configured to be conveyed through a borehole penetrating the earth, wherein the sensor is disposed on the carrier and is configured to perform the measurement for each physical property downhole.

Embodiment 16: The apparatus according to any prior embodiment, wherein the carrier comprises a wireline, a drill string, coiled tubing, or a slickline.

Embodiment 17: The apparatus according to any prior embodiment, wherein the sensor comprises at least one selection from a group consisting or a density sensor, a viscosity sensor, a sound speed sensor, a pressure sensor, and a temperature sensor.

Embodiment 18: The apparatus according to any prior embodiment, further comprising a user interface configured to receive a signal from the processor, the signal comprising the chemical composition of the hydrocarbons of interest.

Embodiment 19: The apparatus according to any prior embodiment, wherein the processor is further configured to generate the prediction function by: obtaining a plurality of measurements of values of different physical properties of samples of hydrocarbons at reservoir temperatures and pressures, each sample having a known chemical composition, to serve as a training set; generating a plurality of composite independent variables comprising two or more variables corresponding to the physical properties of the samples being measured; and performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole.

In support of the teachings herein, various analysis components may be used, including a digital and/or an analog system. For example, the sensors 9, the formation tester 11, the downhole electronics 13, and/or the surface computer processing system 15 may include digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Non-limiting embodiments of carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured. The terms "first" and "second" are used to distinguish elements and are not used to denote a particular order.

The flow diagrams depicted herein are just an example. There may be many variations to these diagrams or the steps (or operations) described therein without departing from the spirit of the invention. For instance, the steps may be performed in a differing order, or steps may be added, deleted or modified. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

In one embodiment, electronics associated with the transducers may be configured to take measurements as the tool moves along the longitudinal axis of the borehole ('axially') using at least one sensor. These measurements may be substantially continuous, which may be defined as being repeated at very small increments of depth, such that the resulting information has sufficient scope and resolution to provide an image of a parameter of interest.

In other embodiments, all or a portion of the electronics may be located elsewhere (e.g., at the surface, or remotely). To perform the treatments during a single trip, the tool may use a high bandwidth transmission to transmit the information acquired by sensors to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "near real-time."

One point of novelty of the systems illustrated in FIGS. 1A & 1B is that the at least one processor may be configured to perform certain methods (discussed below) that are not in the prior art. A surface control system or downhole control system may be configured to control the tool described above and any incorporated sensors and to estimate a parameter of interest according to methods described herein.

Method embodiments may include conducting further operations in the earth formation in dependence upon formation information, estimated properties of the reflector(s), or upon models created using ones of these. Further operations may include at least one of: ii) drilling additional boreholes in the formation; iii) performing additional measurements on the casing and/or the formation; iv) estimating additional parameters of the casing and/or the formation; v) installing equipment in the borehole; vi) evaluating the formation; vii) optimizing present or future development in the formation or in a similar formation; viii) optimizing present or future exploration in the formation or in a similar formation; and x) producing one or more hydrocarbons from the formation.

Estimated parameters of interest may be stored (recorded) as information or visually depicted on a display. The parameters of interest may be transmitted before or after storage or display. For example, information may be transmitted to other downhole components or to the surface for storage, display, or further processing. Aspects of the present disclosure relate to modeling a volume of an earth formation using the estimated parameter of interest, such as, for example, by associating estimated parameter values with portions of the volume of interest to which they correspond, or by representing the boundary and the formation in a global coordinate system. The model of the earth formation generated and maintained in aspects of the disclosure may be implemented as a representation of the earth formation stored as information. The information (e.g., data) may also be transmitted, stored on a non-transitory machine-readable medium, and/or rendered (e.g., visually depicted) on a display.

The processing of the measurements by a processor may occur at the tool, the surface, or at a remote location. The data acquisition may be controlled at least in part by the electronics. Implicit in the control and processing of the data is the use of a computer program on a suitable non-transitory machine readable medium that enables the processors to perform the control and processing. The non-transitory machine readable medium may include ROMs, EPROMs, EEPROMs, flash memories and optical disks. The term processor is intended to include devices such as a field programmable gate array (FPGA).

The term "carrier" as used above means any device, device component, combination of devices, media and/or member that may be used to convey, house, support or otherwise facilitate the use of another device, device component, combination of devices, media and/or member. Exemplary non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (Analog, digital, EM, printed, etc.). The term "processor" or "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on. Thus, a processor may be configured to perform one or more methods as described herein, and configuration of the processor may include operative connection with resident memory and peripherals for executing programmed instructions.

In some embodiments, estimation of the parameter of interest may involve applying a model. The model may include, but is not limited to, (i) a mathematical equation, (ii) an algorithm, (iii) a database of associated parameters, or a combination thereof.

While the foregoing disclosure is directed to the one mode embodiments of the disclosure, various modifications will be apparent to those skilled in the art. It is intended that all variations be embraced by the foregoing disclosure.

The invention claimed is:

1. A method for estimating a presence of oil-based mud (OBM) in a downhole fluid, the method comprising:
generating measurement values downhole by measuring a plurality of gross physical properties of the downhole fluid with at least one sensor, the measurement values comprising at least one measurement value representative of each gross physical property of the plurality; and
estimating with at least one processor a relative concentration of OBM with respect to the downhole fluid by processing the measurement values using a model correlating the measurement values with the relative concentration.

2. The method according to claim 1, wherein measuring the plurality of gross physical properties comprises taking measurements from the downhole fluid in situ.

3. The method according to claim 1, comprising estimating the relative concentration in real-time with respect to generating the measurement values.

4. The method according to claim 1, wherein the model comprises a correlation prediction function mapping the measurement values to the relative concentration.

5. The method of claim 4, wherein the correlation prediction function uses the measurement values as input to predict the relative concentration.

6. The method of claim 5, wherein the correlation prediction function uses only the measurement values as input.

7. The method of claim 4, further comprising generating the correlation prediction function by:
generating a training set by:
obtaining a plurality of sample measurement values for a plurality of gross physical properties for each downhole fluid sample of a plurality of downhole fluid samples, each sample measurement value taken from the corresponding downhole fluid sample of the plurality at a specific temperature and a specific pressure both characteristic of a reservoir,
wherein the sample measurement values comprise at least one sample measurement value representative of each gross physical property of the plurality, and
wherein each downhole fluid sample has a known relative concentration of OBM;
generating a plurality of composite independent variables comprising a plurality of variables corresponding to the plurality of gross physical properties of the plurality of downhole fluid samples; and
estimating the correlation prediction function by performing a regression on the training set for a dependent variable representing the relative concentration of OBM in terms of the composite independent variables.

8. The method according to claim 7, wherein the composite independent variables comprise terms of a multinomial expansion of variables representing the plurality of physical properties being measured.

9. The method according to claim 8, wherein at least one variable in the multinomial expansion is a reciprocal of a physical property being measured.

10. The method according to claim 7, wherein the regression comprises a step forward multiple linear regression with substitution.

11. The method according to claim 1, wherein the plurality of gross physical properties comprises at least two of: i) density, ii) viscosity, iii) sound speed, iv) pressure, and v) temperature.

12. The method according to claim 1, further comprising conveying a carrier having the at least one sensor disposed thereon through a borehole penetrating the earth, wherein measuring each of the plurality of gross physical properties is performed downhole.

13. The method of claim 1 wherein the plurality of gross physical properties consists of density, pressure, and temperature, and the measurement values of density, pressure, and temperature are the only measurement values processed using the model.

14. An apparatus for estimating a presence of oil-based mud (OBM) in a downhole fluid, the apparatus comprising:
   an instrument configured to generate measurement values downhole, the instrument comprising at least one sensor configured to measure a plurality of gross physical properties of the downhole fluid, wherein the measurement values comprise at least one measurement value representative of each gross physical property of the plurality; and
   at least one processor configured to estimate a relative concentration of OBM with respect to the downhole fluid by processing the measurement values using a model correlating the measurement values with the relative concentration.

15. The apparatus of claim 14, further comprising a carrier configured to be conveyed through a borehole penetrating the earth, wherein the at least one sensor is disposed on the carrier and is configured to perform the measuring each of the plurality of gross physical properties downhole.

16. The apparatus of claim 14, wherein the carrier comprises a wireline, a drill string, coiled tubing, or a slickline.

17. The apparatus of claim 14, wherein the apparatus is configured to measure the plurality of gross physical properties from the downhole fluid in situ.

18. The apparatus of claim 14, wherein the apparatus is configured to estimate the relative concentration in real-time with respect to generating the measurement values.

19. The apparatus of claim 14, wherein the model comprises a correlation prediction function mapping the measurement values to the relative concentration.

20. The apparatus of claim 19, wherein the correlation prediction function is configured to use the measurement values as input to predict the relative concentration.

21. The apparatus of claim 20, wherein the correlation prediction function is configured to use only the measurement values as input.

* * * * *